Figure 1:
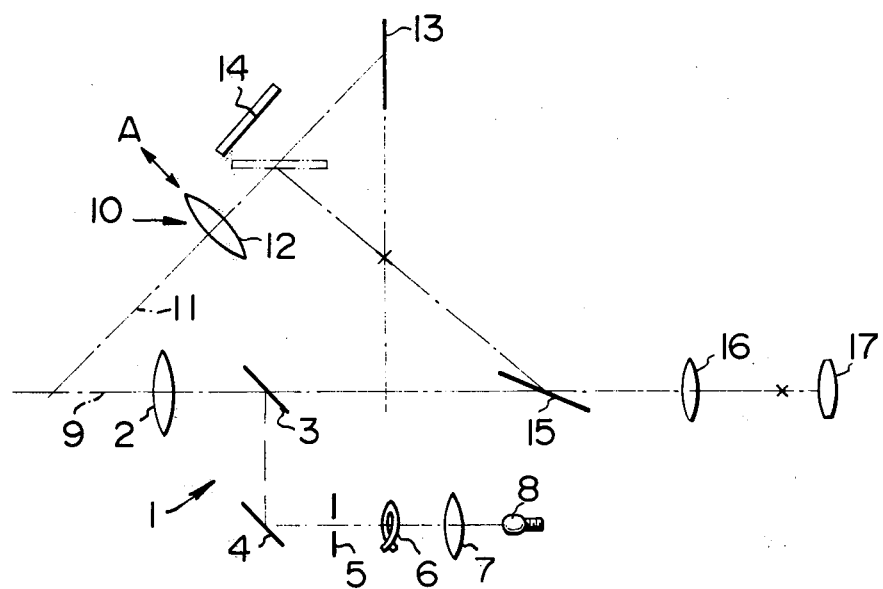

United States Patent [19]

Karasawa

[11] 4,198,143

[45] Apr. 15, 1980

[54] APPARATUS FOR TAKING PHOTOGRAPHS OF SECTIONS OF CRYSTALLINE LENSES IN WHICH LINE FOCUSING MOVES LENS IN ITS OWN PLANE

[75] Inventor: Yukinori Karasawa, Yokohama, Japan

[73] Assignee: Tokyo Kogaku Kikai Kabushiki Kaisha, Tokyo, Japan

[21] Appl. No.: 877,669

[22] Filed: Feb. 14, 1978

[30] Foreign Application Priority Data

Feb. 18, 1977 [JP] Japan .................................. 52/16985

[51] Int. Cl.² .............................................. A61B 3/14
[52] U.S. Cl. ..................... 354/62; 354/160; 354/190; 351/7
[58] Field of Search ................. 351/6, 14, 5–7; 354/62, 160, 189, 190; 350/31, 46–47, 247

[56] References Cited

U.S. PATENT DOCUMENTS 4,019,813   4/1977   Cornsweet .......................... 351/14

FOREIGN PATENT DOCUMENTS 494104   8/1919   France ................................ 354/174
20938    6/1902   United Kingdom ................. 354/189

Primary Examiner—L. T. Hix
Assistant Examiner—Shelley Wade
Attorney, Agent, or Firm—Stevens, Davis, Miller & Mosher

[57] ABSTRACT

Apparatus for photographing sections of crystalline lenses which includes a slit illumination system for illuminating a patient's eye in a slit plane and a photographing system for taking a photographs of the illuminated section of the crystalline lens at an angle of 45° with respect to the plane of slit illumination with a magnification power of one. The photographing system includes a lens which is movable in a direction perpendicular to the photographing optical axis for adjustment of focus.

3 Claims, 2 Drawing Figures

APPARATUS FOR TAKING PHOTOGRAPHS OF SECTIONS OF CRYSTALLINE LENSES IN WHICH LINE FOCUSING MOVES LENS IN ITS OWN PLANE

The present invention relates to an apparatus for taking photographs of sections of crystalline lenses in patient's eyes.

Conventionally, known apparatus for taking photographs of sections of crystalline lenses include a slit illumination system for illuminating a patient's eye in a slit plane and a photographing system for taking photographs of the illuminated section of the crystalline lens at an angle with respect to the plane of slit illumination. In this type of apparatus, it is possible to have the image of the crystalline lens section focused throughout the film plane by locating the film in such a manner that the plane of the film intersects the plane of the illumination slit along a line which lies in a plane containing the major plane of the photographing lens. Typically, a one magnification power optical system can be provided by an arrangement in which the film plane is so located that it intersects the plane of the slit illumination at the right angle and the photographing lens is positioned at the middle point of the photographing optical path with the major plane thereof located in such a manner that it contains the line of intersection between the film plane and the slit illumination plane.

In general, the photographing optical system is positioned in this type of apparatus at a predetermined relationship with respect to the slit illumination system when the apparatus is assembled so that adjustment of focus is substantially accomplished. However, it is still necessary to provide means for fine adjustment of focus in view of the facts that there is a cornea of the patient's eye between the illuminated section of the crystalline lens and the photographing film and that the curvatures of the cornea may be different among patients so that apparent positions of the illuminated sections may also be different among patients.

Referring to the one magnification power optical system, the photographing lens must be located at a specific position with respect to the object and the image. More specifically, the distances between the center of the lens and the front and rear focal points between the front focal point and the object, and the rear focal point and the image must all be equal each other. Further, with respect to a specific lens, the distance between the object and the image is the smallest when the magnification power is one. Therefore, it is impossible in such an optical system to move the photographing lens axially for focusing in accordance with a displacement of the object. Focusing may be performed in such an apparatus by moving the photographing optical system as a whole so that the distance between the object and the image is adjusted while maintaining the relationship between the photographing lens and the image plane. However, such a solution is not recommendable because very complicated mechanisms are required for the purpose.

It is therefore an object of the present invention to provide simple focusing means for an apparatus for taking photographs of crystalline lenses.

Another object of the present invention is to provide a one magnification power optical system for an apparatus for taking photographs of crystalline lenses, with simple means for focusing.

According to the present invention, the above and other object can be accomplished by an apparatus for photographing sections of crystalline lenses which comprises a slit illumination system for illuminating the crystalline lens in a slit plane, and a photographing optical system having an optical axis intersecting said slit plane at an angle of substantially 45° and a film plane intersecting said slit plane at an angle of 90°, said photographing optical system including photographing lens means positioned in said optical axis to provide a magnification power of one, said photographing lens means being movable in a plane which is perpendicular both to the slit plane and the film plane and in a direction perpendicular to the optical axis. For example, the photographing lens means may include a lens tube which eccentrically carries a photographing lens so that the aforementioned movement is produced simply by rotating the lens tube. Alternately, the photographing lens means may be mounted on housing means for slidable movement in the aforementioned direction.

In an optical system having perpendicularly intersecting slit plane and film plane, and a photographing optical axis which intersects both the slit plane and the film plane at an angle of 45°, with a photographing lens positioned in the optical axis to provide a magnification power of one, any displacement of the object can be compensated for by a movement of the photographing lens in the direction perpendicular to the optical axis because such movement of the photographing lens produces a corresponding movement of the image in the same direction and the distance between the object and the image can be maintained substantially constant. Displacement of the object to be viewed, in the specific embodiment being the human eye, can occur due to variations from person to person. Therefore, the object to be viewed, the eye, could be located above or below the slit plane 9 resulting in a corresponding defocusing of the image on the photographic plate 13. Compensation of this type of defocusing is accomplished by the aforesaid movement of the photograph lens in the direction perpendicular to the optical axis. Therefore, any change due to changes in the curvature of the cornea and the refractive index of crystalline lens is sufficiently compensated for. Precisely speaking, such movement of the photographing lens may cause a displacement of the point of intersection between the optical axis and the film plane and may produce a slight misalignment between the major plane of the photographing lens and the line of intersection between the slit plane and the film plane. Further, the magnification power may be slightly changed. However, for the purpose of the apparatus, the movement of the photographing lens is considered as being sufficient in providing a satisfactory focusing.

Figure 2:
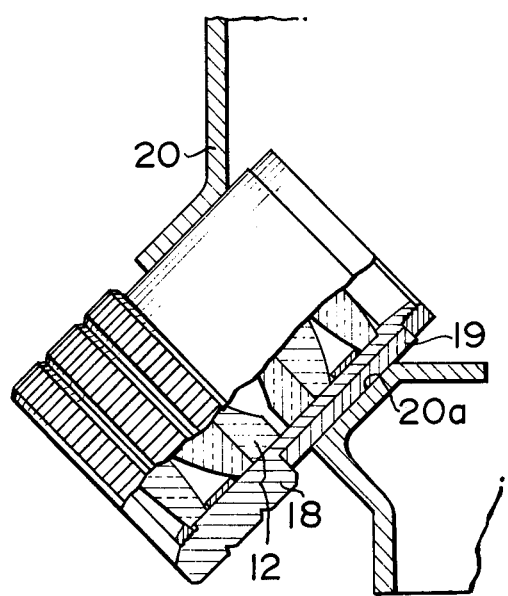

The above and other objects and features of the present invention will become apparent from the following descriptions of a preferred embodiment taking reference to the accompanying drawings, in which:

FIG. 1 is a diagrammatical view of an optical system embodying the feature of the present invention; and FIG. 2 is a fragmentary sectional view showing the focusing mechanism in accordance with one embodiment of the present invention.

Referring to the drawings, particularly to FIG. 1, the apparatus shown therein includes a slit illumination system 1 which includes a projecting lens 2, reflecting mirrors 3 and 4, a slit mask 5 having a slit, a photographing light source such as a xenon lamp 6, a condenser lens 7 and a illumination light source 8 whereby the light which has passed through the slit in the mask 5 is projected along the slit plane 9 which is perpendicular to the plane of drawing.

The apparatus further includes a photographing optical system 10 having a photographing lens 12 which is disposed with the optical axis 11 intersecting the slit plane 9 at an angle of 45°. The photographing optical system 10 further includes a film 13 which is disposed in a plane which is perpendicular to the slit plane 9 and also to the plane of drawing. The photographing lens 12 is located at the middle position of the photographing optical path and has a major plane lying in a plane which includes the line of intersection between the slit plane 9 and the film plane.

In the photographing optical path, there is retractably disposed a reflecting mirror 14 for reflecting a light which has passed through the lens 12 toward a finder system comprising a reflecting mirror 15, a relay lens 16 and an eye lens 17. For photographing, the mirror 14 is retracted to the position shown by solid lines in FIG. 1.

According to the feature of the present invention, the photographing lens 12 is movable at least in the plane of drawing in the direction as shown by an arrow A for the purpose of focusing. In FIG. 2, there is shown an example of lens mount which allows such movement of the photographing lens 12. In this example, the lens 12 is housed in a lens tube 18 which is received in an eccentric tube 19. The lens tube 18 is secured to the eccentric tube 19 so that they are rotated as a unit. The lens tube 18 is mounted on a camera housing 20 by being rotatably supported at the eccentric tube 19 on a cylindrical bearing surface 20a provided in the housing 20. Thus, it will be noted that a rotation of the lens tube 18 produces a transverse displacement of the optical axis 11 with a component of movement as shown by the arrow A in FIG. 1. It should of course be noted that the lens tube 18 may be mounted on the camera housing 20 for slidable movement in the plane of drawing and in the direction perpendicular to the optical axis 11. For the purpose, a suitable sliding guide may be provided on the housing 20.

The invention has thus been shown and described with reference to a specific embodiment, however, it should be noted that the invention is in no way limited to the details of the illustrated arrangements but changes and modifications may be made without departing from the scope of the appended claims.

I claim:

1. Apparatus for photographing sections of crystalline lenses which comprises a slit illumination system for illuminating the crystalline lens in a slit plane, and a photographing optical system having an optical axis intersecting said slit plane at an angle of substantially 45° and a film plane intersecting said slit plane at an angle of 90°, said photographing optical system including photographing lens means positioned in said optical axis to provide a magnification power of one, said photographing lens means being movable in a plane which is perpendicular both to the slit plane and the film plane and in a direction perpendicular to the optical axis.

2. Apparatus in accordance with claim 1 in which said photographing lens means includes a lens and a lens tube which eccentrically carries the lens on a housing.

3. Apparatus in accordance with claim 2 in which said lens tube is mounted on the housing through an eccentric tube.

* * * * *